(12) United States Patent
Hwang et al.

(10) Patent No.: US 7,854,723 B2
(45) Date of Patent: Dec. 21, 2010

(54) NEEDLE SHIELD ASSEMBLY HAVING HINGED NEEDLE SHIELD

(75) Inventors: Charles G. Hwang, Ridgewood, NJ (US); Bradley M. Wilkinson, North Haledon, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 251 days.

(21) Appl. No.: 11/772,980

(22) Filed: Jul. 3, 2007

(65) Prior Publication Data

US 2008/0033362 A1 Feb. 7, 2008

Related U.S. Application Data

(63) Continuation of application No. 10/495,319, filed as application No. PCT/US02/13581 on Apr. 30, 2002, now abandoned.

(60) Provisional application No. 60/335,907, filed on Nov. 15, 2001, provisional application No. 60/292,680, filed on May 22, 2001.

(51) Int. Cl.
*A61M 5/178* (2006.01)
(52) U.S. Cl. .................... 604/164.08; 604/533
(58) Field of Classification Search ...............
604/164.01–164.08, 174–180, 192, 263, 604/284, 533–539
See application file for complete search history.

(56) References Cited

U.S. PATENT DOCUMENTS

| 1,779,451 A | 10/1930 | Sponsel |
| 2,004,050 A | 6/1935 | Kerk |
| 2,700,385 A | 1/1955 | Ortiz |
| 2,836,942 A | 6/1958 | Miskel |
| 2,854,976 A | 10/1958 | Heydrich |
| 2,953,243 A | 9/1960 | Roehr |
| 3,021,942 A | 2/1962 | Hamilton |
| 3,073,307 A | 1/1963 | Stevens |
| 3,074,542 A | 1/1963 | Myerson et al. |
| 3,255,873 A | 6/1966 | Speelman |
| 3,294,231 A | 12/1966 | Vanderbeck |

(Continued)

FOREIGN PATENT DOCUMENTS

EP 0995456 A1 4/2000

(Continued)

OTHER PUBLICATIONS

Extended European Search Report mailed on Nov. 27, 2008 for European Patent Application No. 08166118.3.

*Primary Examiner*—Nicholas D Lucchesi
*Assistant Examiner*—Gerald Landry, II
(74) *Attorney, Agent, or Firm*—Jeanne P. Lukasavage; Diehl Servilla LLC

(57) ABSTRACT

A needle shield assembly including a hinged needle shield is provided. A ramp is provided in proximity to a hinge that connects the needle shield to base assembly. The ramp is preferably flexible, and, if compressed, resiliently urges the needle shield to a preferred angular position with respect to a syringe. The needle shield is movable between a fully opened position where it is canted at an angle with respect to the syringe and a closed position in which it envelops the needle. One or more locking elements are preferably provided on the needle shield for maintaining it in a locked, needle protecting position.

13 Claims, 14 Drawing Sheets

U.S. PATENT DOCUMENTS

| | | |
|---|---|---|
| 3,323,523 A | 6/1967 | Scislowicz at al. |
| 3,329,146 A | 7/1967 | Waldman, Jr. |
| 3,333,682 A | 8/1967 | Burke |
| 3,367,488 A | 2/1968 | Hamilton |
| 3,485,239 A | 12/1969 | Vanderbeck |
| 3,537,452 A | 11/1970 | Wilks |
| 3,610,240 A | 10/1971 | Harautuneian |
| 3,658,061 A | 4/1972 | Hall |
| 3,828,775 A | 8/1974 | Armel |
| 3,890,971 A | 6/1975 | Leeson et al. |
| 3,904,033 A | 9/1975 | Haerr |
| 3,934,722 A | 1/1976 | Goldberg |
| 3,968,876 A | 7/1976 | Brookfield |
| 4,113,090 A | 9/1978 | Carstens |
| 4,139,009 A | 2/1979 | Alvarez |
| 4,175,008 A | 11/1979 | White |
| 4,300,678 A | 11/1981 | Gyure et al. |
| RE31,086 E | 11/1982 | Johnson, Jr. et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gherardi |
| 4,664,259 A | 5/1987 | Landis |
| 4,664,654 A | 5/1987 | Strauss |
| 4,671,408 A | 6/1987 | Raines et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byne et al. |
| 4,826,491 A | 5/1989 | Schramm |
| 4,838,871 A | 6/1989 | Luther |
| 4,842,587 A | 6/1989 | Poncy |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,900,309 A | 2/1990 | Netherton et al. |
| 4,909,791 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,966,591 A | 10/1990 | Yuen |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,154,285 A | 10/1992 | Hollister |
| 5,188,611 A | 2/1993 | Orgain |
| 5,197,954 A | 3/1993 | Cameron |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,277,311 A | 1/1994 | Hollister |
| 5,312,369 A | 5/1994 | Arcusin et al. |
| 5,314,411 A * | 5/1994 | Bierman et al. ............. 604/174 |
| 5,401,251 A | 3/1995 | Hui |
| 5,405,332 A | 4/1995 | Opalek |
| 5,423,765 A | 6/1995 | Hollister |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,509,907 A | 4/1996 | Bevilacqua |
| 5,533,984 A | 7/1996 | Parmigiani |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,681,295 A | 10/1997 | Gyure et al. |
| 5,693,022 A | 12/1997 | Haynes |
| 5,702,369 A | 12/1997 | Mercereau |
| 5,733,265 A | 3/1998 | Bachman et al. |
| 5,807,351 A | 9/1998 | Kashmer |
| 5,836,920 A | 11/1998 | Robertson |
| 5,868,716 A * | 2/1999 | Sweeney et al. ............. 604/263 |
| 5,885,249 A | 3/1999 | Irisawa |
| 5,910,130 A | 6/1999 | Caizza et al. |
| 5,913,846 A | 6/1999 | Szabo |
| 5,993,426 A | 11/1999 | Hollister |
| 6,077,253 A | 6/2000 | Cosme |
| 6,080,137 A | 6/2000 | Pike |
| 6,120,482 A | 9/2000 | Szabo |
| 6,139,533 A | 10/2000 | Xia et al. |
| RE37,110 E | 3/2001 | Hollister |
| RE37,252 E | 7/2001 | Hollister |

| | | | |
|---|---|---|---|
| 6,319,232 B1 | 11/2001 | Kashmer | |
| 6,328,713 B1 | 12/2001 | Hollister | |
| 6,334,857 B1 | 1/2002 | Hollister et al. | |
| 6,517,522 B1 * | 2/2003 | Bell et al. | 604/263 |
| 6,592,556 B1 * | 7/2003 | Thorne | 604/192 |
| 6,695,819 B2 * | 2/2004 | Kobayashi | 604/192 |
| 6,699,217 B2 | 3/2004 | Bennett et al. | |
| 2001/0039401 A1 * | 11/2001 | Ferguson et al. | 604/198 |
| 2002/0072711 A1 * | 6/2002 | Cindrich | 604/164.08 |
| 2004/0215154 A1 | 10/2004 | Hwang et al. | |
| 2005/0054986 A1 | 3/2005 | Simpson et al. | |
| 2005/0065481 A1 | 3/2005 | Hauri et al. | |
| 2005/0065482 A1 | 3/2005 | Hauri et al. | |

FOREIGN PATENT DOCUMENTS

| | | |
|---|---|---|
| GB | 1233302 | 5/1971 |
| GB | 2239604 | 7/1991 |
| GB | 2239607 | 7/1991 |
| GB | 2240273 | 7/1991 |
| GB | 2240477 | 8/1991 |
| WO | WO 87/07162 | 12/1987 |
| WO | WO 90/01348 | 2/1990 |
| WO | WO 91/09637 | 7/1991 |
| WO | WO 91/09638 | 7/1991 |
| WO | WO 91/09639 | 7/1991 |
| WO | WO 93/16745 | 9/1993 |

* cited by examiner

NEEDLE SHIELD ASSEMBLY HAVING HINGED NEEDLE SHIELD

This application is a continuation of U.S. Ser. No. 10/495,319, filed on May 11, 2004 which is a 371 of PCT/US02/13581 filed Apr. 30, 2002 which claims the benefit of U.S. Provisional Application Nos. 60/292,680 filed May 22, 2001 and 60/355,907 filed Feb. 11, 2002.

FIELD OF THE INVENTION

The field of the invention relates to needle shield assemblies for medical devices such as hypodermic needles.

BACKGROUND OF THE INVENTION

Accidental needle sticks from used hypodermic needles can transmit disease. Various types of needle shields have been designed to reduce the possibility of accidental sticks.

A needle shield that is hinged near the base of the needle has the advantage of allowing one handed needle reshielding. Accordingly, a number of prior art needle shield assemblies have been developed that include such needle shields.

Various means have been provided for locking a hinged needle shield in the closed, needle protecting, position. Deflectable members have been provided in the needle shield for engaging the needle upon shielding and preventing subsequent unshielding of the needle. Such members trap the needle within the needle shield. Locking has also been accomplished by locking engagement of the needle shield with the needle support structure.

SUMMARY OF THE INVENTION

A needle shield assembly in accordance with the present invention includes a base assembly having a hub and a base member connected to the hub. A needle cannula having a proximal portion secured to the hub and a distal portion extending from the hub defining a longitudinal axis is provided. A coupling on the base assembly includes a channel transverse to the longitudinal axis of the needle cannula and having an opening therein. A projection on the base assembly has a distal end proximal to the channel and a top surface inclined outwardly with respect to the longitudinal axis in a distal direction. A needle shield having a cavity therein is connected to the coupling at the channel. The needle shield is capable of rotating from an open position wherein the needle cannula is exposed for use, to a closed needle protecting position wherein at least the distal portion of the needle cannula is in the cavity. The needle shield preferably includes a proximal end portion having a top surface wherein the top surface is able to contact the projection on the base assembly when the needle shield is rotated to the open position. The needle shield assembly may include a projection that is flexibly mounted to the base assembly and able to be contacted by the needle shield when the needle shield is in the open position. The needle shield assembly may include structure for locking the needle shield in the closed needle protecting position.

Another embodiment of the needle shield assembly of the present invention includes a base assembly having a hub, a base member connected to the hub and a coupling on the base member. A needle cannula having a proximal portion secured to the hub and a distal portion extending from the hub defining a longitudinal axis is provided. The coupling includes a channel transverse to the longitudinal axis of the needle cannula. A flexible projection is provided on the base assembly. The projection is positioned proximally with respect to the coupling. A needle shield having a cavity therein is hingedly connected to the base assembly at the channel. The needle shield is capable of rotating from an open position wherein the needle cannula is exposed to a closed needle protecting position. The projection of this embodiment preferably includes a proximal end pivotably coupled to the base assembly in a distally extending tab. The channel includes a proximally facing opening and the tab includes a surface in opposed relation to the channel opening. The tab includes a top surface that is inclined outwardly with respect to the longitudinal axis in a distal direction.

Another embodiment of the needle shield assembly of the present invention includes a base assembly having a hub, a base member connected to the hub, and a coupling on the base member. A needle cannula having a proximal portion secured to the hub and a distal portion extending from the hub defining a longitudinal axis is provided. A projection on the base assembly is positioned proximally with respect to the coupling and includes a top finger-guiding surface inclined outwardly with respect to the longitudinal axis in a distal direction. A needle shield having a cavity therein is hingedly connected to the coupling. The needle shield is capable of rotating from an open position wherein the needle cannula is exposed, to a closed needle protecting position wherein at least the distal portion of the needle cannula is in the cavity. The needle shield is able to contact the projection when the needle shield is rotated to the open position. The needle shield assembly can also have a projection which is flexibly mounted to the base assembly. The projection on the base may be deflectable and can include a proximal end coupled to the base and a distally extending tab, wherein the tab is able to contact both the base member and the needle shield when the needle shield is in the open position. One way of hingedly connecting the needle shield to the coupling is by providing a channel in the coupling which is transverse to the longitudinal axis of the needle cannula. The channel has a channel opening for engaging a pin on the proximal end of the needle shield so that the needle shield may rotate around the channel from the open position to the closed needle protecting position.

DETAILED DESCRIPTION OF THE DRAWINGS

Figure 1:
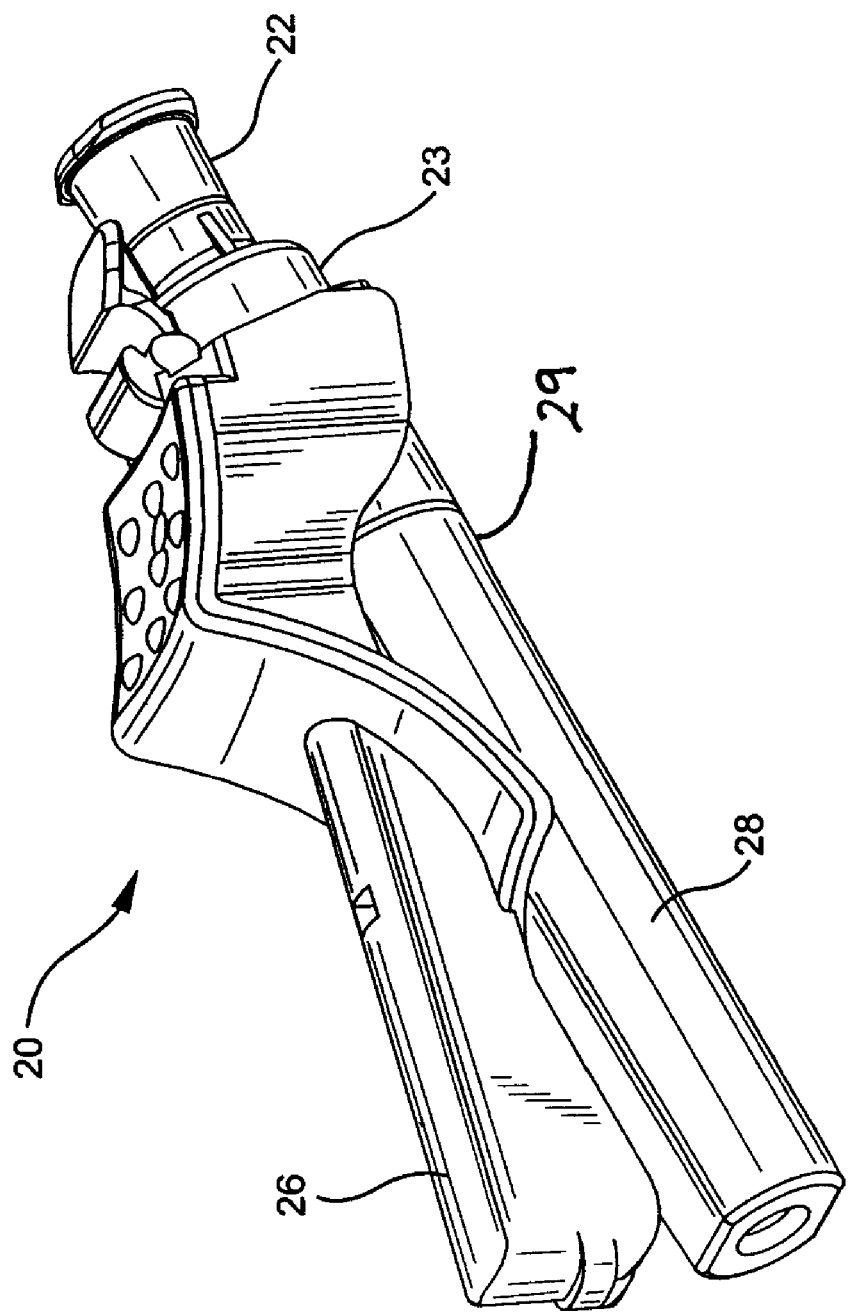
FIG. 1 is a top perspective view of a needle shield assembly according to the invention.
Figure 2:
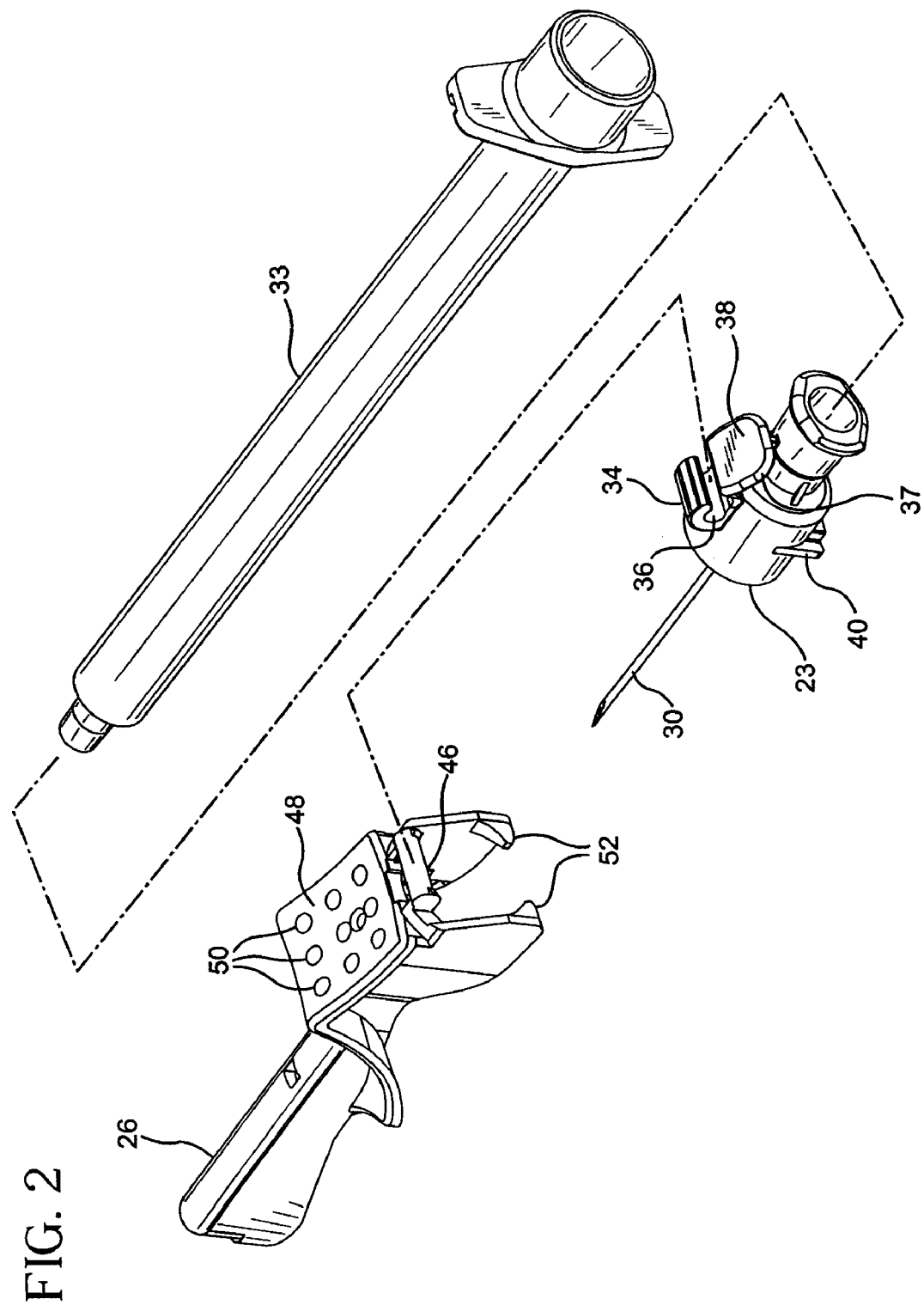
FIG. 2 is an exploded top perspective view showing a medical device including a syringe barrel, a needle hub and base member, and a needle shield.

While this invention is satisfied by embodiments in many different forms, there are shown in the drawings and will be herein described in detail preferred embodiments of the invention with the understanding that the present disclosure is to be considered exemplary of the principles of the invention and is not intended to limit the scope of the invention to these embodiments illustrated. The scope of the invention will be measured by the appended claims and their equivalents. As used throughout this specification and as seen in the Figures, the term "distal" refers to the end of the needle assembly furthest from the person holding the needle assembly and the term "proximal" refers to the end of the needle assembly closest to the person holding of the needle assembly.

Figure 6:
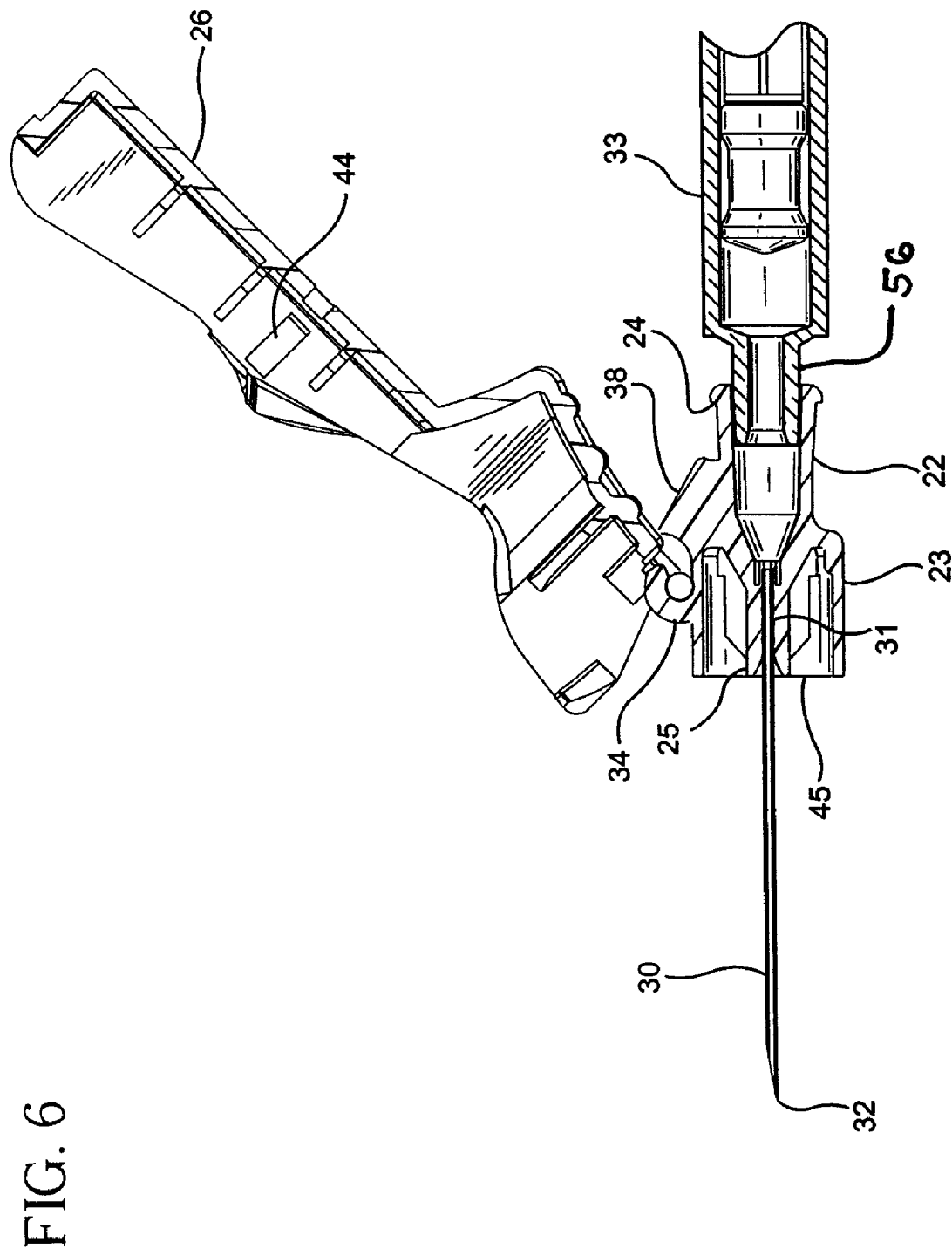
FIG. 6 is a cross-sectional view of the medical device of FIG. 4 showing the needle shield in the fully open position.
Figure 7:
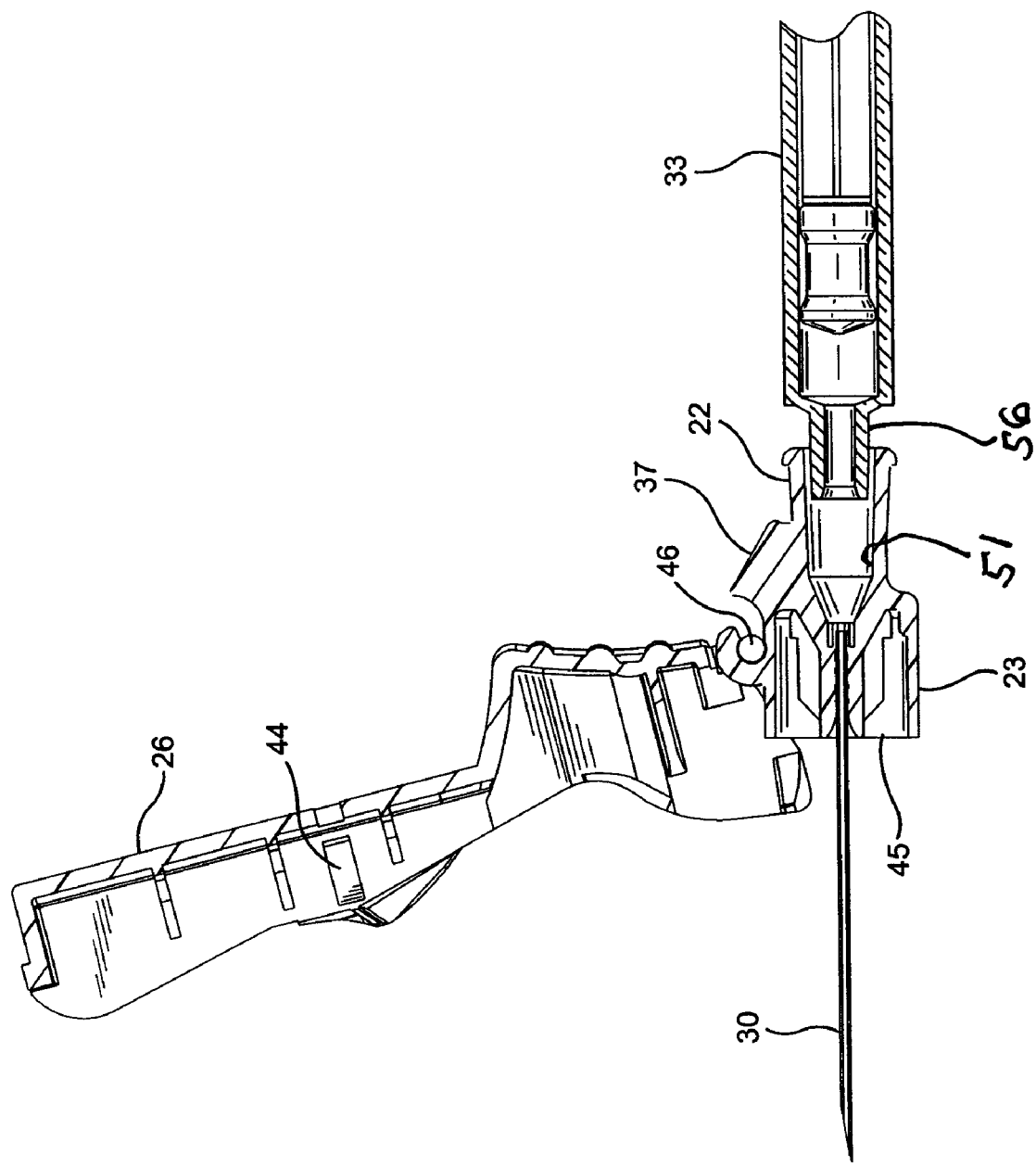
FIG. 7 is a cross-sectional view of the medical device of FIG. 4 showing the needle shield rotated partially towards the closed position.
Figure 8:
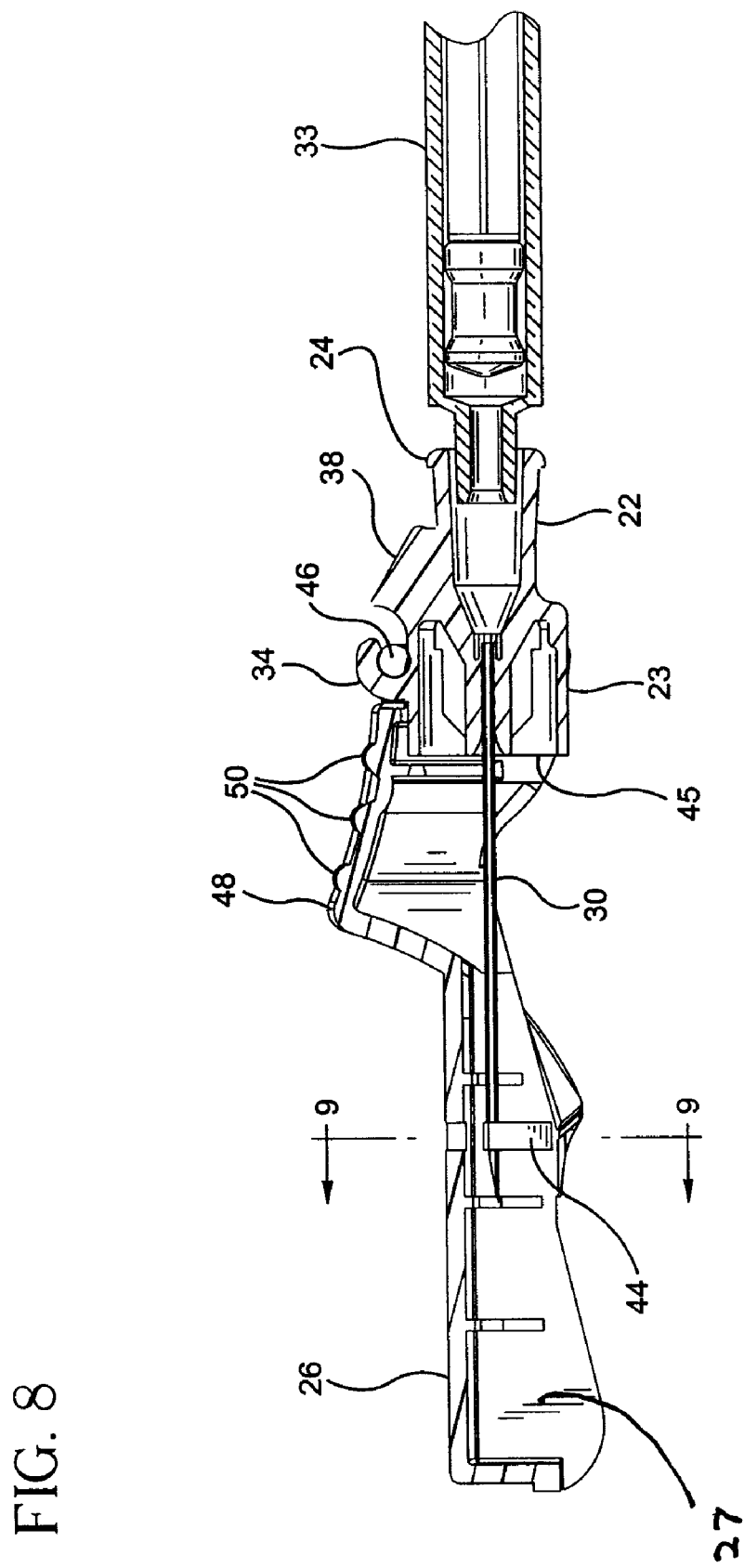
FIG. 8 is a cross-sectional view of the medical device of FIG. 4 showing the needle shield in the closed position.

Referring to FIG. 1, a needle shield assembly 20 includes a hub 22, a base member 23, a needle shield 26 and an elongate hollow needle cover 28. A needle cannula 30 is attached to the needle hub. As shown in FIGS. 6-8, the needle cannula 30 includes a proximal end 31 and a distal end 32. In this embodiment, the distal end of the needle cannula preferably includes a sharpened tip. Blunt cannula are, however, known to the art and are often used to inject liquid into the injection site of an IV set. The principles of the invention are applicable to assemblies including blunt cannulas as well as needle cannulas having sharpened tips and various other known needle tip shapes.

The hub 22 includes a proximal end 24 and a distal end 25 that is connected to the proximal end of the needle cannula. The base member may be and is preferably integral with the hub, as shown, or joined thereto by an interference fit, adhesives, ultrasonic welding and the like. All such hub/base member assemblies are within the purview of the present invention. The proximal end of the hub defines a connector for connecting the needle shield assembly to a medical device such as a syringe 33. In this embodiment the proximal end of the hub includes a frusto-conically shaped cavity 51 which frictionally engages a frusto-conically shaped elongate tip 56 on syringe 33. Various assemblies for connecting needle assemblies to syringes are known and are considered within the purview of the present invention.

Figure 3:
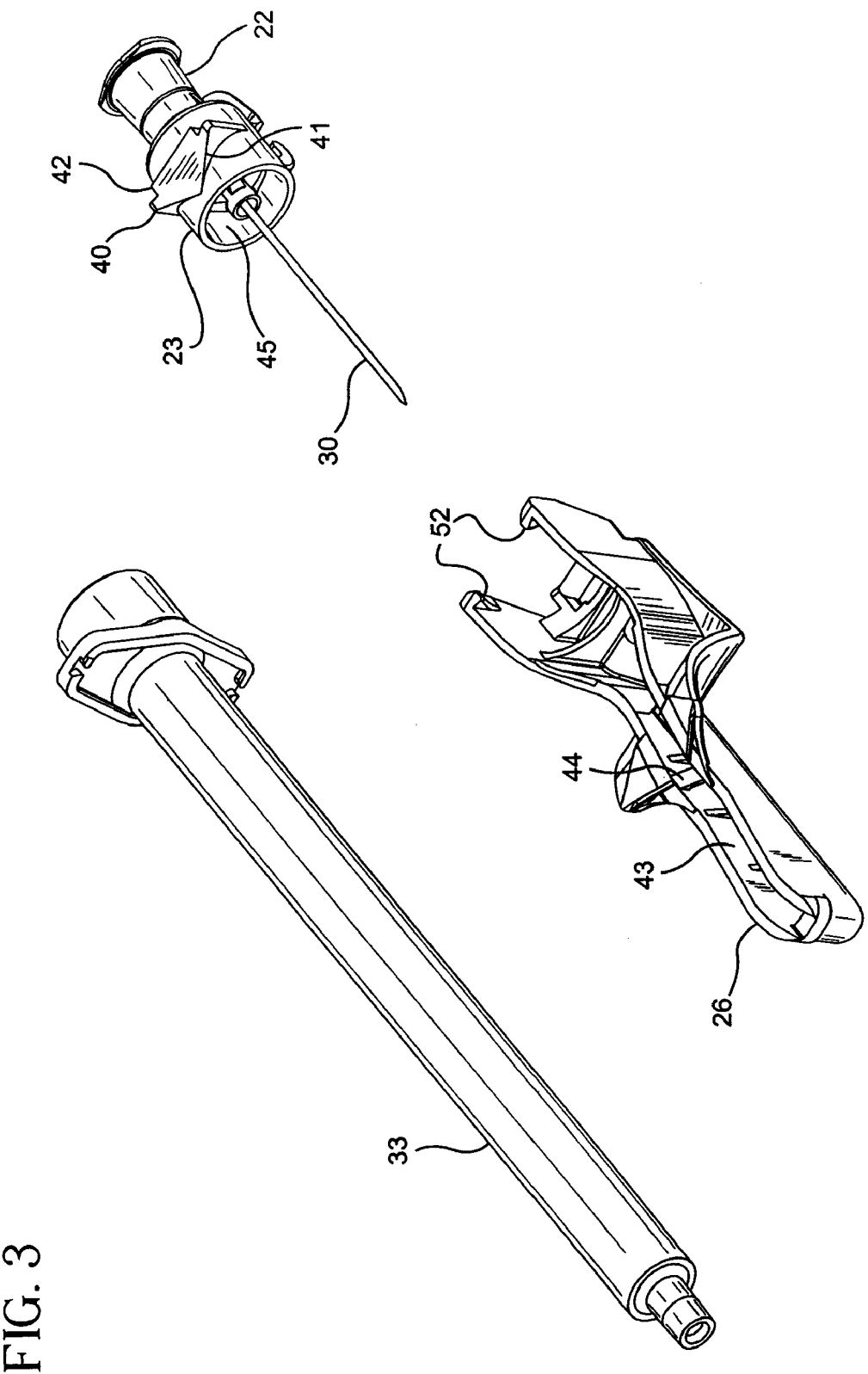
FIG. 3 is an exploded bottom perspective view of the medical device of FIG. 2.
Figure 4:
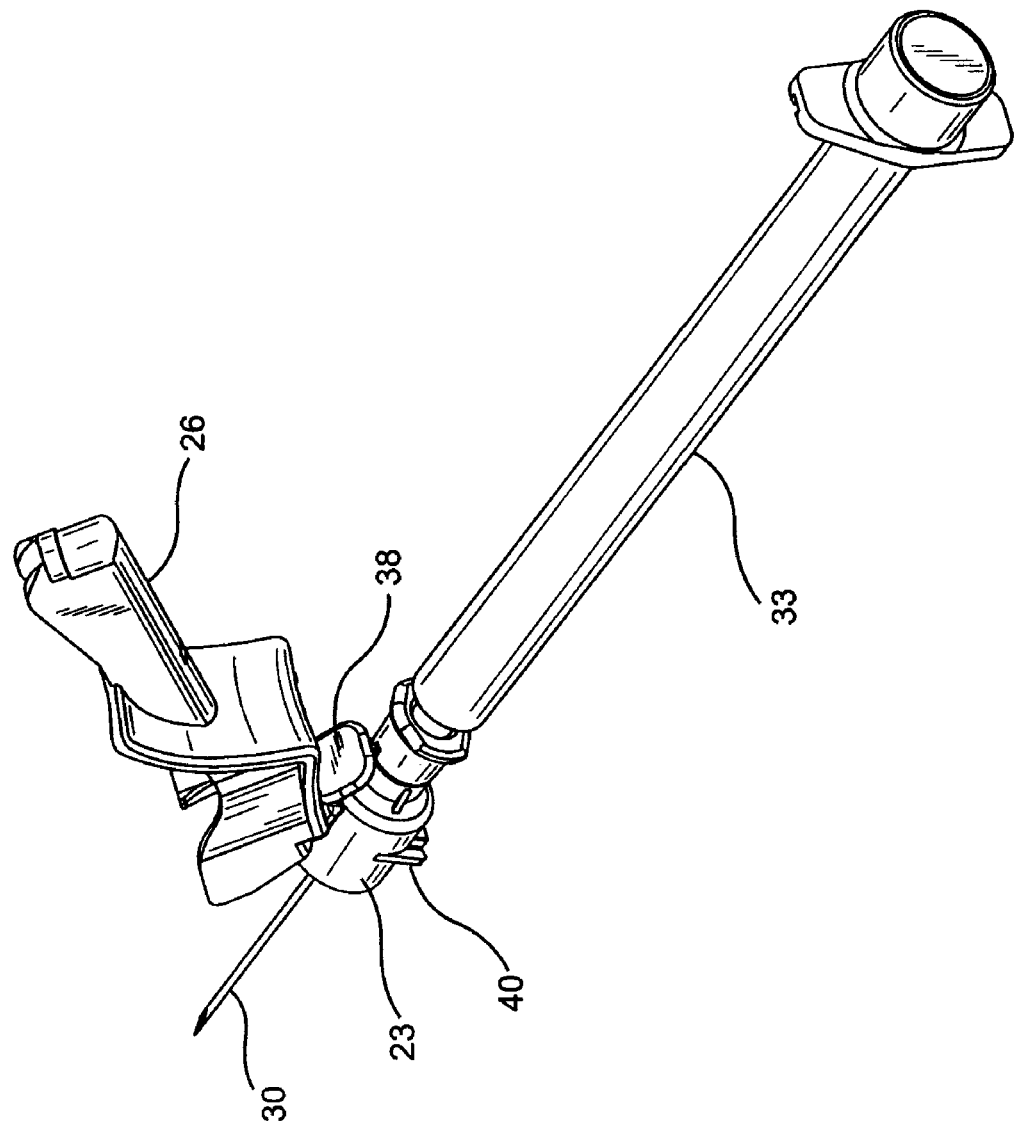
FIG. 4 is a top perspective view of a medical device showing the needle shield in the open position.
Figure 5:
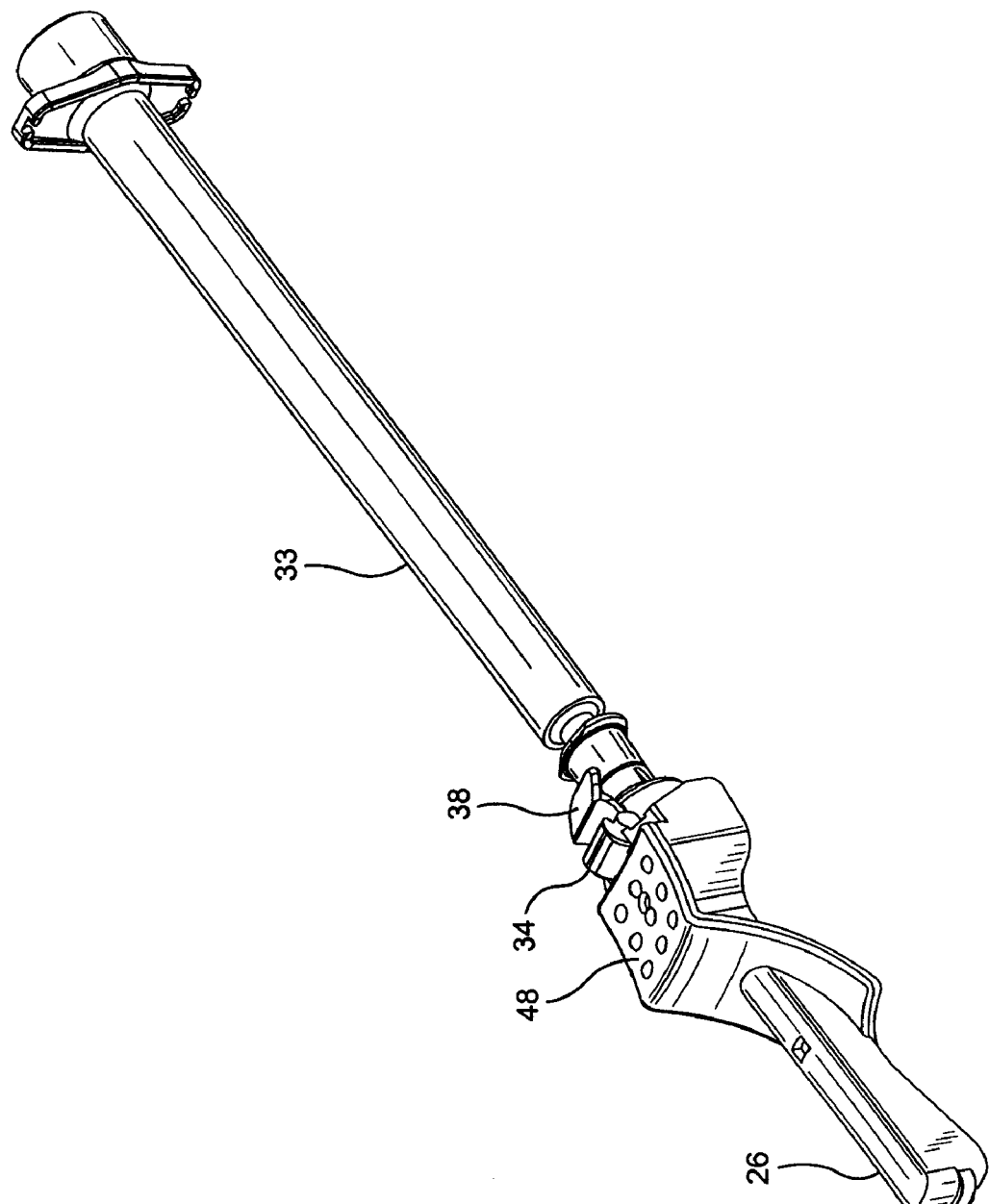
FIG. 5 is a top perspective view of the medical device of FIG. 4 showing the needle shield in the closed position.
Figure 12:
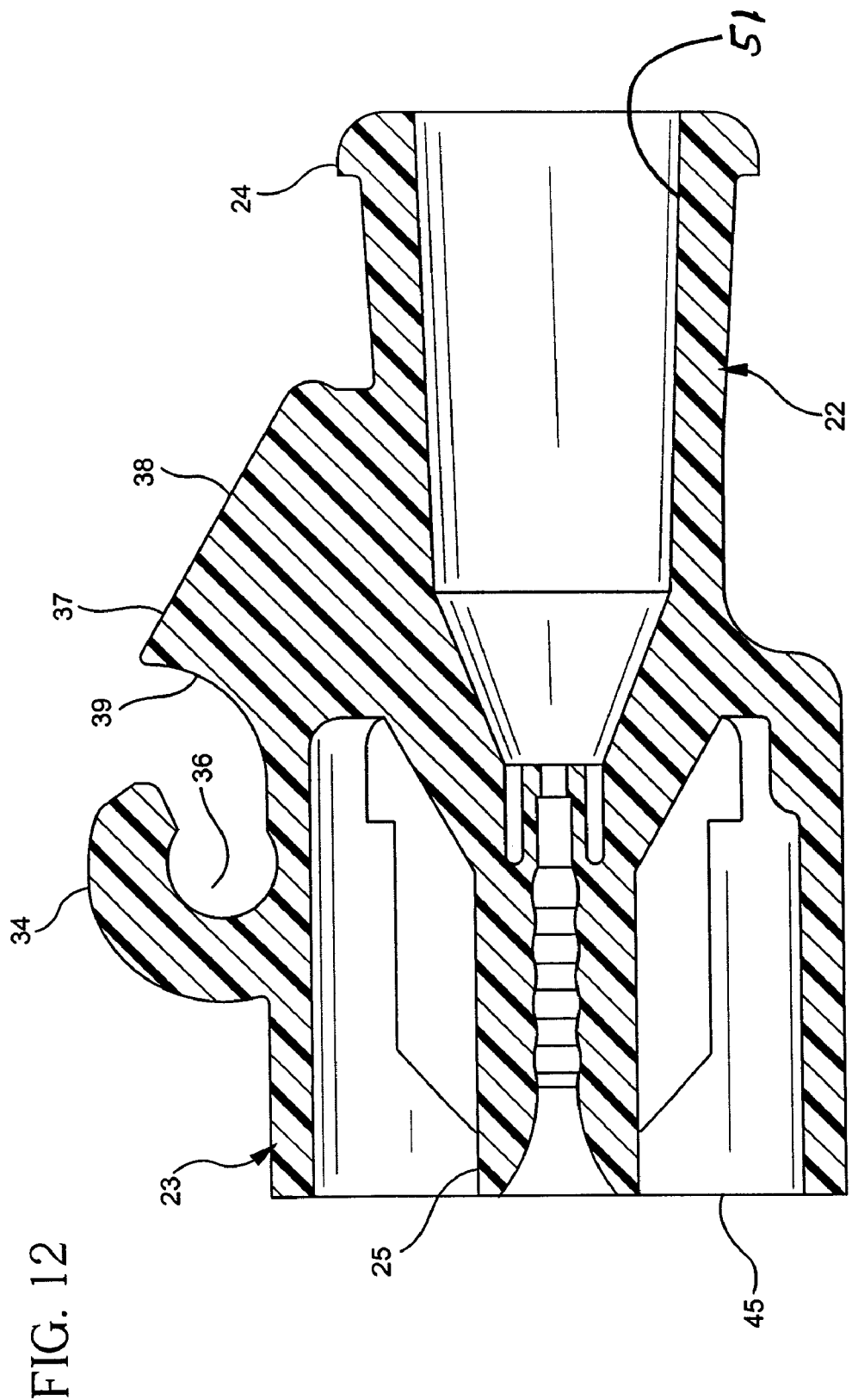
FIG. 12 is a cross-sectional view showing the needle hub and base member as an integral assembly.

Base member 23 comprises a coupling, which in this embodiment includes a hook shaped projection 34 and a channel 36 having an arcuate surface as defined by the projection 34 and the body of the base member 23. The channel includes an opening that preferably faces proximally. A finger guiding projection 37 is located proximal to the channel 36 and the channel opening, and includes a top surface 38 that is inclined outwardly in the distal direction. The top surface is inclined outwardly in the views shown in FIGS. 6-8. The projection 37 also includes a curved distal end face 39 that is in substantially opposing relation to the channel opening, as shown in FIG. 12. Top surface 38 is shown as a relatively flat surface, however, it is within the purview of the present invention to include top surfaces of various shapes such as convex or concave or combinations thereof. The base member 23 further includes a projection 40 including a pair of inclined surfaces 41. The proximal end of the projection 40 includes a pair of notches 42. FIG. 3 shows these elements.

Elongate hollow needle cover 28 is provided to protect the needle cannula before the needle shield assembly of the present invention is used for its intended purpose. Elongate hollow needle cover 28 includes an open proximal end 29 which is releasably engaged to the base so that the needle cannula is in the hollow needle cover. The base member is preferably generally cylindrical, and preferably includes a distal opening 45 for receiving open proximal end 29 of hollow needle cover 28 in a preferably snap-fit engaging manner. The snap fit engaging structure can comprise one or more projections or recesses on the needle shield and on the base member.

Figure 9:
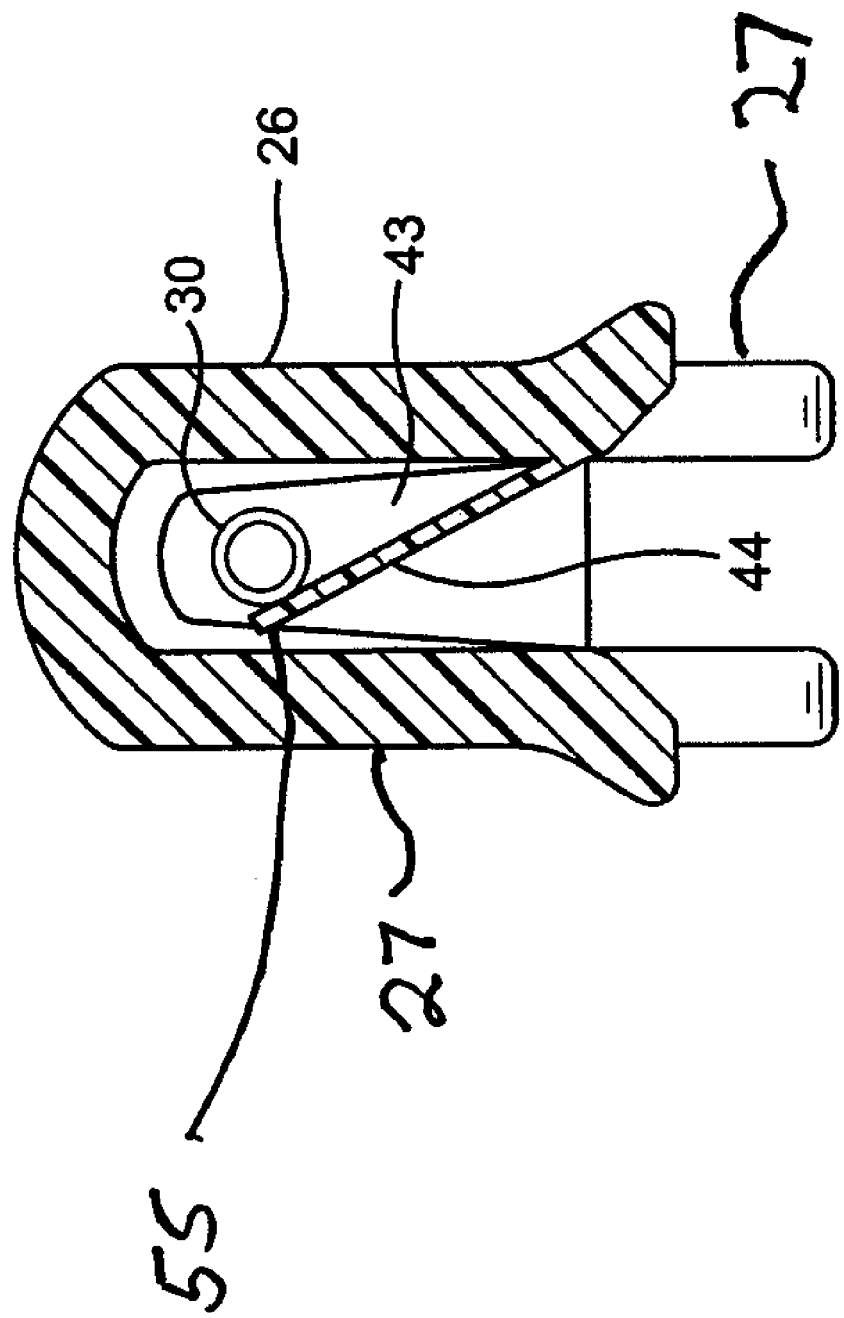
FIG. 9 is a cross-sectional view of the medical device of FIG. 8 taken along line 6-6.
Figure 10:
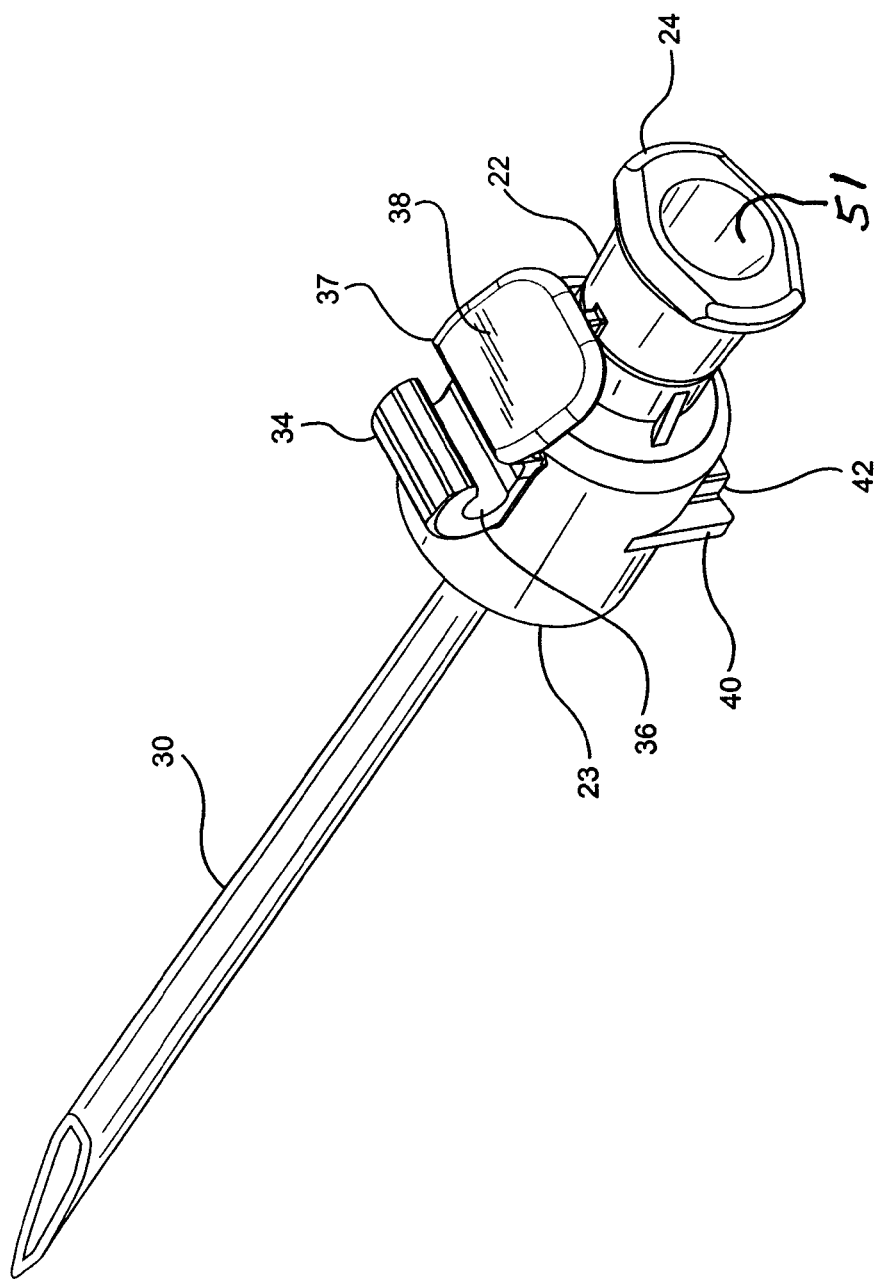
FIG. 10 is a top perspective view showing the base member, hub and needle of the needle shield assembly of the present invention.
Figure 11:
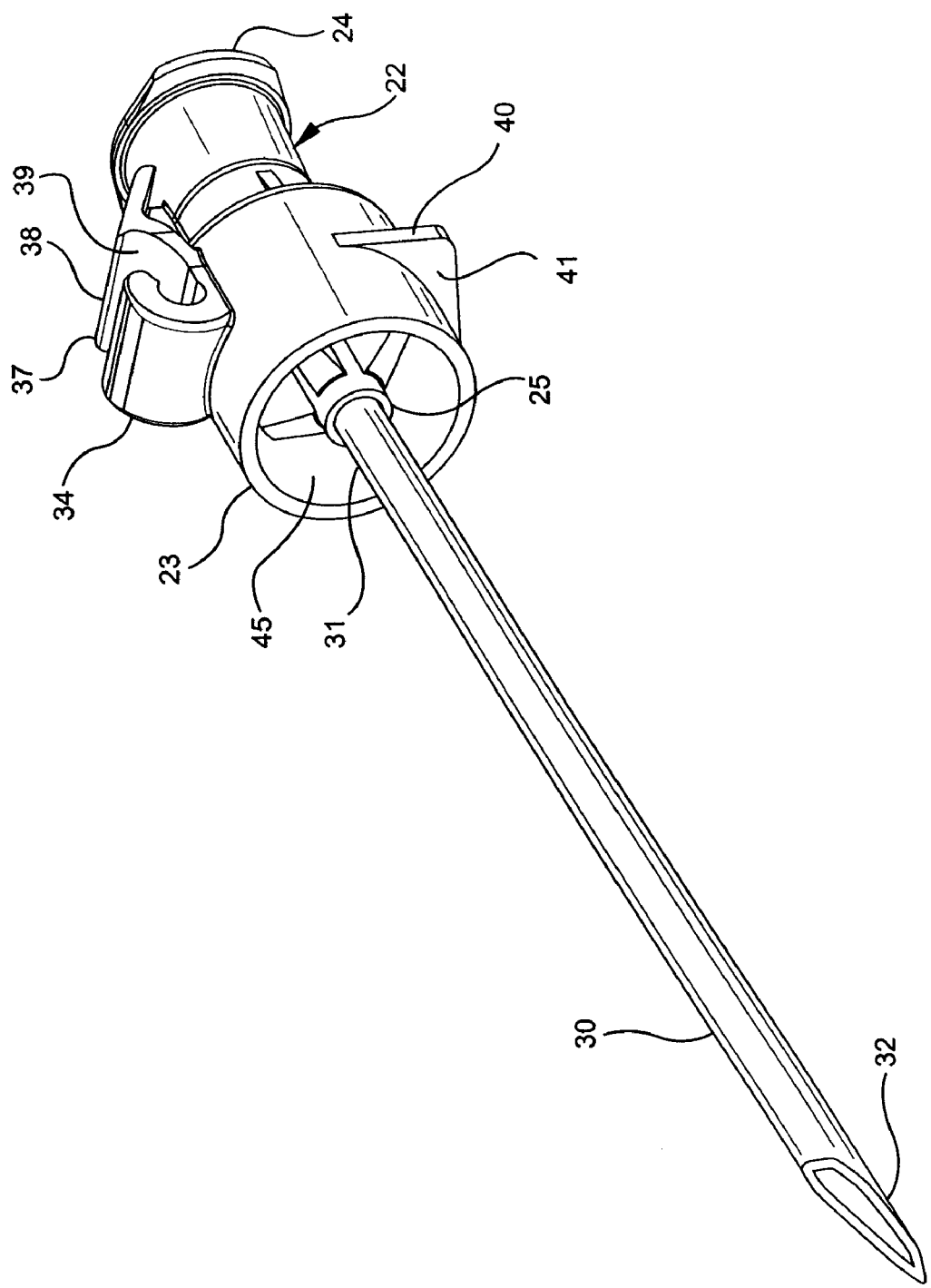
FIG. 11 is another top perspective view showing the base member, hub and needle of the needle shield assembly of FIG. 10 from a different angle.

Needle shield 26 includes a cavity 43 for enveloping needle 30. At least one projection 44 extends from a side wall of the needle shield into the cavity 43. The projection is deflectable towards the side wall of the needle shield 26 when engaged by the needle 30. Once the needle is far enough within the cavity 43 to be positioned beyond free end 55 of the projection 44, as shown in FIGS. 8 and 9, the projection springs back to its original position. The projection is preferably long enough so that any attempt to move the needle cannula out of the cavity will cause free end 55 of projection 44 to contact the interior surface of the cavity to resist re-exposure of the needle cannula. The projection is preferably integral with the sidewall of the needle shield and coupled thereto near the opening of the cavity 43. The projection may include a living hinge at or near the point where it extends from the side wall.

A pin 46 is coupled to the proximal end of the needle shield as shown in FIGS. 2, 6, 7 and 8. Pin 46 is of such dimensions that it can be snapped into channel 36 in the base member 23 and retained therein by the channel walls. With pin 46 in channel 36, the needle shield is capable of rotating from an open position wherein the needle cannula is exposed to a closed needle protecting position wherein at least the distal end of the needle cannula is in the cavity of the needle shield. Preferably most or all of the exposed needle cannula should be within in the cavity when the needle shield is in the closed position. While needle shield 26 is readily coupled to base member 24 during manufacture of needle shield assembly 20, these components are configured to make it very difficult to dislodge the hinge pin 46 from the channel 36 as the shield is rotated in either direction. There are many structures to hingedly connect the needle shield to the base member such as a living hinge, a flexible connection, and various structures which function in the hinge-like manner and all of these structures are within the purview of the present invention. The pin and channel structure described herein is representative of these many possibilities. It is preferred that the base member and the hub be integrally formed of a plastic material. A wide variety of plastic materials can be used to form the base and the hub. Polypropylene is preferred and especially useful for forming structure of the channel opening and the pin on the needle shield to make a hingeable assembly with enough friction to keep the needle shield from moving freely under its own weight and requiring some force to change position of the needle shield when it is not locked in the closed needle protecting position.

The needle shield 26 further includes a top surface 48 defining a finger guide area near pin 46. The top surface of the needle shield is preferably curved between its proximal and distal ends, and preferably includes projections 50 or similar features to facilitate rotating the needle shield with a finger. The needle shield includes a pair of opposing projections 52 that extend from the sidewalls of the needle shield near the proximal end of the needle shield. Each of the projections 52 includes an inclined proximal surface and a distal surface that is substantially perpendicular to the side walls of the needle shield. The projections are spaced such that the proximal surfaces thereof are engageable with the inclined surfaces 41 of the base member projection 40 as the needle shield is rotated about the pin 46. As the side walls near the proximal end of the needle shield are flexible, continued rotation of the needle shield causes the side walls to flex outwardly until the projections 52 snap into the notches 42 in the base member projection 40. While two locking projections and notches are provided for locking the needle shield in the closed needle protecting position, it will be appreciated that one or more locking mechanism may be used. Also it is not necessary to lock the shield to both the needle and the base member, and the shield may be locked to one of the base member or the needle to provide locking means for the present invention.

The needle shield assembly may be integral with the medical device or removably coupled thereto. The assembly 20 may be provided to the end user in a sterile package (not shown). Once removed from the package, it is in the form shown in FIG. 1. and may be coupled to a medical device such as syringe 33. The needle shield 26 is then rotated in the proximal direction about the hinge pin 46 and the needle cover 28 is removed. The medical device is then ready for use when the needle shield 26 extends generally proximally at an acute angle with respect to the medical device, as shown in FIG. 6. In the preferred embodiment, this acute angle is about forty-five degrees as measured between the longitudinal axis of the syringe/needle and the longitudinal axis of needle shield 26. Projection 37 limits the rotation of the needle shield in a proximal direction, and allows it to be positioned where the medical device can be easily used and the shield can be readily utilized. Inclined top surface 38 of projection 37 functions as a finger-guiding ramp in that it directs the user's finger outwardly to facilitate rotating the shield from the open position shown in FIG. 6 to the closed needle protecting position shown in FIG. 8. Projection 37 is a very important feature of the present invention. In addition to facilitating the rotation of the needle shield to the closed needle protecting position, it redirects the digital force being supplied by the user's fingertip from a distally directed axial force to distally outwardly directed force. This redirection of the digital force reduces the potential for the digital force to overcome the frictional engagement of the hub cavity and the syringe tip and cause the needle assembly to become disengaged from the syringe while the needle shield is being rotated into the closed needle protecting position. The shield 26 is locked to the needle by the projection 44 and to the base member by engagement of the projections 52 with the base member projection 40. It is then substantially non-reusable, and can be discarded in accordance with procedures used for discarding sharps.

Needle shield 26 preferably includes parallel sidewalls 27. In applications with very long needle cannula it may be desirable to have the parallel sidewalls at the distal end of the needle shield be longer to define a deeper cavity than at the proximal end of the needle shield. The needle shield can still get close to the longitudinal axis of the needle, as illustrated in FIG. 1, while further isolating the distal end of the needle cannula after the needle is in the closed needle protecting position.

Figure 13:
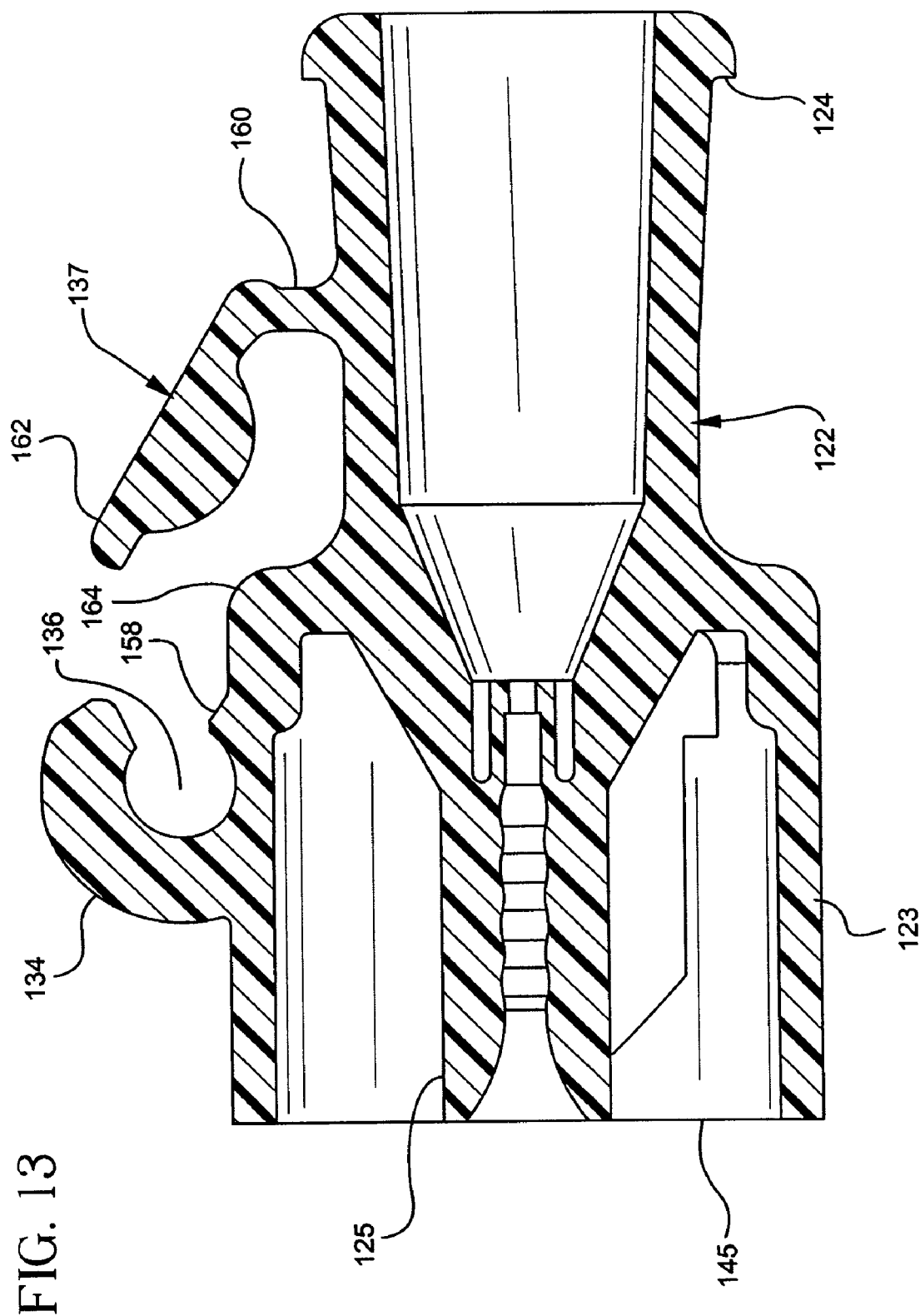
FIG. 13 is a cross-sectional view of a needle hub and base member according to a second embodiment of the present invention.

FIG. 13 shows a needle hub 122 in accordance with a second and preferred embodiment of the invention. Needle hub 122 includes a proximal end 124 and a distal end 125. The distal end 125 is adapted to receive the proximal end of a needle cannula. The proximal end 124 thereof defines a connector for connecting the hub to a medical device such as a syringe.

A base member 123 is integral with the hub 122, though alternatively it could be joined thereto by an interference fit, adhesives, ultrasonic welding, or the like. The base member includes a hook-shaped projection 134 and a channel 136 having an arcuate surface defined by the projection 134 on the body of the base member. A ridge 158 extends radially outwardly from the base member 123 and extends towards the free end of the projection 134. The base member 123 preferably but not necessarily includes an opening 145 for receiving the proximal end of a needle cover (not shown).

A resilient projection 137 extends from the base member. The projection 137 comprises a hinged or cantilevered area represented by a hinge 160 that is integral with the base member and a tab 162 that extends generally in the direction of the hook-shaped projection 134. Hinge 160 can be a living hinge or a portion configured to facilitate bending. The tab, in this embodiment, is in opposing relation to the opening to the channel 136 when the projection is unflexed, as shown in FIG. 13. A shoulder 164 is defined by the base member 123. The projection 137 is configured such that the tab 162 preferably contacts the shoulder of the base member 123 when projection 137 is urged towards the longitudinal axis of the hub.

Figure 14:
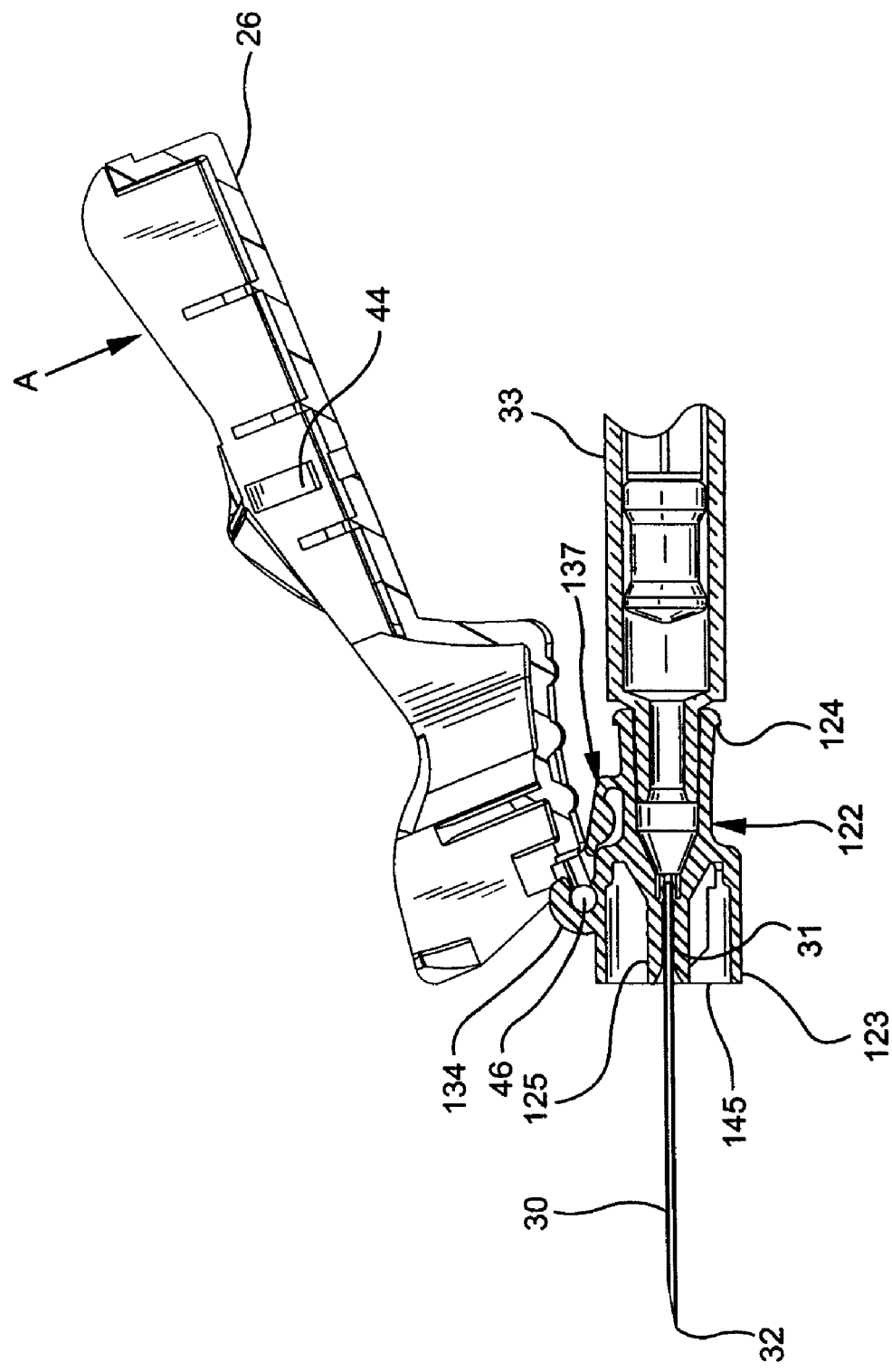
FIG. 14 is a cross-sectional view of a needle shield assembly according to the second embodiment of the invention with the needle shield thereof being forced to a fully open position.

Referring to FIG. 14, a needle shield 26 as described above is pivotably attached to the base member 123. The shield is shown rotated back towards the syringe 33 by application of force A. The top surface of the needle shield engages the tab 162 and displaces projection 137 since it is not a rigid structure. This flexibility is an important feature of the present embodiment since it reduces the possibility of dislodging the hinge pin 46 from the channel 136 if the needle shield is urged against projection 137. A projection such as ridge 158 also helps prevent displacement or dislodging of the hinge pin from the channel during normal use. As the tab 162 tends to assume its resting position shown in FIG. 13, it will urge the needle shield 26 about the hinge pin 46 from the position shown in FIG. 14 to the preferred position, where projection 137 is unstressed, which is about a forty-five degree angle from the longitudinal axis of the needle and syringe 33. While in this position, which corresponds to that shown in FIG. 6 of the first-described embodiment, the user is easily able to rotate the needle shield 26 into the needle-protecting position while employing only one hand. There is sufficient space between the finger guide area 48 of the needle shield and the inclined surface of the tab 162 to allow the insertion of finger tip by most users, thereby initiating shield rotation. The shield is appropriately contoured elsewhere to protect the user while facilitating use of the shield.

Resilient projection 137 is an important feature of the present invention. It provides guidance to the user's finger tip to guide it radially distally outwardly into a smooth transition onto the needle shield. Also, it is intended that the user should not apply excessive force, such as Force A in FIG. 14, to the needle shield. Excessive and unnecessary force applied to the needle shield will force the needle shield against projection 137 which, if not resilient, could act as a fulcrum to magnify forces on hinge pin 46 which could possibly break it or dislodge it from channel 136. However, because projection 137 is resilient, it pivots inwardly to reduce forces being applied to hinge pin 46. When the excessive and unnecessary force is discontinued, the resilient projection pivots outwardly moving the needle shield with it to the desired needle shield position for shielding the needle after use.

What is claimed is:

1. A needle shield assembly comprising:
   a base assembly including a hub and a base member connected to said hub;
   a needle cannula having a proximal portion secured to said hub and a distal portion extending from said hub, said needle cannula having a longitudinal axis;
   said base member comprising a coupling, said coupling including a channel transverse to said longitudinal axis of said needle cannula and a channel opening;
   said coupling further including a projection having a distal end proximal to and extending from said channel opening and a top surface connected to said distal end of the projection, said top surface being inclined outwardly with respect to said longitudinal axis in the distal direction; and
   a needle shield having a cavity therein and a pin positioned for rotational movement in said channel, and having a proximal end portion having a top surface, wherein said needle shield is hingedly connected to said coupling by said pin at said channel, said needle shield capable of rotating from an open position wherein said needle cannula is exposed, to a closed needle protecting position wherein at least the distal position of said needle cannula is in said cavity, and wherein said top surface of said needle shield is able to contact said projection when said needle shield is rotated to said open position.

2. The needle shield assembly of claim 1 including:
   at least one locking projection on said needle shield;
   at least one locking projection on said base; and
   at least one notch on said base, wherein said needle shield locking projection engages with said base locking projection and locks into said notch to lock said needle shield in said closed needle protecting position.

3. The needle shield assembly of claim 1 wherein said projection is flexibly mounted to said base assembly, said top surface of said needle shield being able to contact said projection when said needle shield is in said open position.

4. The needle shield assembly of claim 1 wherein said hub, said base member and said coupling are integrally formed of one-piece construction of plastic material.

5. The needle shield assembly of claim 4 wherein said plastic material comprises polypropylene.

6. A needle shield assembly comprising:
   a base assembly including a hub and a base member connected to said hub;
   a needle cannula having a proximal portion secured to said hub and a distal portion extending from said hub, said needle cannula having a longitudinal axis;
   said base member comprising a coupling, said coupling including a channel transverse to said longitudinal axis of said needle cannula and a channel opening;
   said coupling further including a projection located proximal to said channel having a proximal end coupled to said base assembly and a tab extending from the proximal end and being inclined outwardly with respect to said longitudinal axis in the distal direction; and
   a needle shield having a cavity therein and a pin positioned for rotational movement in said channel, and having a proximal end portion having a top surface, wherein said needle shield is hingedly connected to said coupling by said pin at said channel, said needle shield capable of rotating from an open position wherein said needle cannula is exposed, to a closed needle protecting position wherein at least the distal position of said needle cannula is in said cavity, and wherein said top surface of said needle shield is able to contact said tab when said needle shield is rotated to said open position.

7. The needle shield assembly of claim 6 wherein said tab is flexible and able to contact said base member.

8. The needle shield assembly of claim 7 wherein said projection is coupled to said base assembly by a living hinge.

9. The needle shield assembly of claim 8 including a pin on said needle shield, said pin being positioned for rotational movement in said channel.

10. The needle shield assembly of claim 8 wherein said needle shield includes a locking member for locking said needle shield in said closed needle protecting position.

11. The needle shield assembly of claim 6 including:
    at least one locking projection on said needle shield;
    at least one locking projection on said base; and
    at least one notch on said base, wherein said needle shield locking projection engages with said base locking projection and locks into said notch to lock said needle shield in said closed needle protecting position.

12. The needle shield assembly of claim 6 wherein said hub, said base member and said coupling are integrally formed of one-piece construction of plastic material.

13. The needle shield assembly of claim 12 wherein said plastic material comprises polypropylene.

* * * * *